United States Patent [19]

Bettinger

[11] Patent Number: 5,474,527
[45] Date of Patent: Dec. 12, 1995

[54] POSITIVE DISPLACEMENT TRANSDERMAL SYSTEM

[76] Inventor: David S. Bettinger, 8030 Coventry, Grosse Ile, Mich. 48138

[21] Appl. No.: 272,075

[22] Filed: Jul. 8, 1994

Related U.S. Application Data

[63] Continuation-in-part of Ser. No. 38,285, Mar. 29, 1993, Pat. No. 5,427,585.

[51] Int. Cl.$^6$ .................................................. A61F 13/00
[52] U.S. Cl. .................................................................. 604/19
[58] Field of Search ................................. 604/20, 890.1, 604/891.1, 892.1, 82, 416, 304–308; 222/95; 424/447–449

[56] References Cited

U.S. PATENT DOCUMENTS 5,053,001  10/1991  Reller et al. ............................. 604/20
5,188,260  2/1993  Bettinger ................................. 222/95

Primary Examiner—C. Fred Rosenbaum
Assistant Examiner—Manuel Mendez

[57] ABSTRACT

A microprocessor controlled transdermal medication patch system wherein said medication is dispensed internally by positive displacement from multiple reservoirs within said patch so as to vary the drug selection, sequence, and concentration and thereby the regimen and release rate. In a preferred embodiment, electric resistance heating elements activate multiple heat-shrink polymer reservoirs to dispence beneficial fluids into a common absorbent layer for transdermal passage.

9 Claims, 1 Drawing Sheet

POSITIVE DISPLACEMENT TRANSDERMAL SYSTEM

CROSS-REFERENCES TO RELATED APPLICATIONS

This is a continuation in part of application 08/038,285 filed 03/29/93 and now U.S. Pat. No. 5,427,585 D. Betringer Art Unit 3309.

STATEMENT AS TO RIGHTS TO INVENTIONS MADE UNDER FEDERALLY-SPONSORED RESEARCH AND DEVELOPMENT

No Federally-sponsored work was associated with this invention.

BACKGROUND OF THE INVENTION

1. Field of Invention

This invention generally relates to a patch for dispensing parenteral fluid medication through the skin and more particularly to a patch which has its regimen electronically controlled by timing and by sensors.

In general patches have found usage for the ambulatory patient requiring an extended regimen of a single drug such as for a chronic condition or for birth control.

Microchip control of drug dispensing and physiological sensing is now used in hospital ICUs. As these technologies are downsized and move to ambulatory patient devices, the microchip processing evolves for a transdermal system that is worn to control a chronic condition but that will also respond to trauma. Such a multi-response transdermal system requires a multi-drug transdermal patch that allows discretionary, independent selection of drug, sequence, and potency.

Chronic conditions such as hormone deficiency which rely on continuous medication would benefit from a transdermal regimen which was moderated to daily and weekly biorythyms. Other chronic conditions such as diabetes, panic, or pain attacks may require intermittent administration to match severity and duration. Other conditions such as cardiovascular may require selection and sequencing from a variety of drugs to counter the precise nature of an attack.

Non-medical situations may require multiple doses during the operational life of a transdermal patch. An example of this would be a commercial pilot who may require a stimulant at intervals during a long flight to remain alert, based on physiological sensing.

2. Description of the Prior Art

Drug Selection: There are two branches to prior art on multiple reservoir transdermal dispensing: (1) those patches that have multiple reservoirs but simultaneously dispense from all their reservoirs such as Reller, and (2) patches that offer drug selectivity. 8 External selection includes (1) injection into the patch by Jacobsen and by Mathiesen, (2) selection by reservoir replacement by Newman and by Sabalis, and (3) selection by a central controller from multiple patches with differing drugs by Newman. There are two branches to prior art on selective multi-drug transdermal dispensing: (1) passive migration by diffusion, dilution, or migration such as Helber, and (2) assisted migration by electrophoteresis and electroosmosis such as Sibalis in #4,921,475.

Because of the need for uniform transfer over the exposed skin area, electrophoteresis requires complex electrode arrangements that have not addressed multi-drug selection.

Helber is a manual unit and despite its selection capability has no provision for electronic control.

Both passive and assisted migration are inefficient from a space standpoint and are not likely to be able to accommodate more than a few drugs per patch.

Sequence Selection: All prior art discloses predetermined sequencing. None disclose variable sequencing.

Dosage Rate Selection: User activated systems such as Helber et al provide only continuous medication after activation. Helber et al states in line 35 that "only a single release rate results per system."

Electrophoteric systems are capable of varying the dosage level by varying the electrical characteristics. However, true multi-drug responsive systems must be capable of dispensing mixture of drugs with differing size molecules and sensing the pharmacokinetic reactions and modifying the administration to respond perhaps by more aggressive therapy. This implies a reselection of drug and regimen, a response not possible in the prior art.

Prior art on graduated delivery of medication include electrophoteric systems, multi-polymer, and rate-limited membrane systems. Only the electrophoteric system is compliant to varying patient needs in a microchip controlled environment. Prior systems possessed no positive dispensing capability. Their electrodes were placed within each reservoir to assist migration such as Reller. No common reservoir or common electrode was possible. This lack make for a complex system limited in the number of drugs that could be efficiently administered.

None of these systems has a zero level of medication when the drug laden patch is attached except Hebler.

None of these systems features medication dispensing internal to the patch to allow variation in drug choice and concentration, which controls release rate.

SUMMARY OF THE INVENTION

1. Objects of the Invention

It is a general object of this invention to overcome the aforementioned drawbacks of prior art transdermal medication dispensing systems.

It is a general object of this invention to provide a transdermal patch improvement to fully utilize sensor driven microprocessor control.

It is another general object of this invention to teach selectivity of drug, sequence, and dosage rate by the use of a plurality of micro-dispensers that dispense internal to the patch. In iontophoretic systems this common reservoir can be equipped with an arrangement of electrodes to assure uniform administration through the skin.

It is another object of this invention to teach the use within a patch of heat-shrink polymer micro-dispensers.

It is another object of this invention to provide a transdermal patch which can administer all intravenous, intramuscular, or subcutaneous drugs for extended-regimens including hormones, cardiovascular, and psychotropics, and for responsive remediation including analgesics, stimulants, and clotting agents. It is still another object of this invention to provide a transdermal medication system capable of variable multi-drug sequencing.

It is yet another object of this invention to provide varying dosage rates by varying the number of micro-dispenser units activated in relation to the fluid carrier units activated.

2. Features of the Invention

In keeping with these objects and others which will become apparent hereinafter, one feature of this invention resides, briefly stated, in a microprocessor controlled transdermal medication patch wherein the improvement comprises the addition of a plurality of segregated reservoirs capable of dispensing by positive displacement into at least one common reservoir internal to said patch. The segregated reservoirs have at least one closable outlet through which a beneficial fluid is dispensed. Said common reservoir consists of an absorbent layer of material.

A first embodiment of the invention concerns said segregated reservoirs which comprise at least one wall of heat-shrink polymer material, and an electrical resistance heating element which when activated results in a reduction in the interior volume of said reservoir forcing said beneficial fluid through said outlet by positive displacement.

A further refinement of this embodiment concerns the heat shrink polymer reservoir wall which achieves in its post-dispensing state a relaxed shape in which the opposing internal surfaces are adjacent and parallel so as to minimize any residual undispensed charge.

A second embodiment concerns said patch wherein said reservoir heating element vaporizes a liquid and expels said beneficial fluid through said outlet by positive displacement.

A third embodiment concerns the improved patch wherein said segregated reservoirs comprise a piezoelectric driven piston to dispense said beneficial fluid by said positive displacement.

A fourth embodiment concerns the improved patch wherein said segregated reservoirs comprise an electric solenoid driven piston to dispense said beneficial fluid by positive displacement.

A fifth embodiment concerns the improved patch wherein said segregated reservoirs comprise and electric powered pump to dispense said beneficial fluid by positive displacement.

A sixth embodiment concerns the improved patch wherein said common reservoir comprises at least one iontophoretic electrode.

DESCRIPTION OF THE PREFERRED EMBODIMENTS

Figure 1:
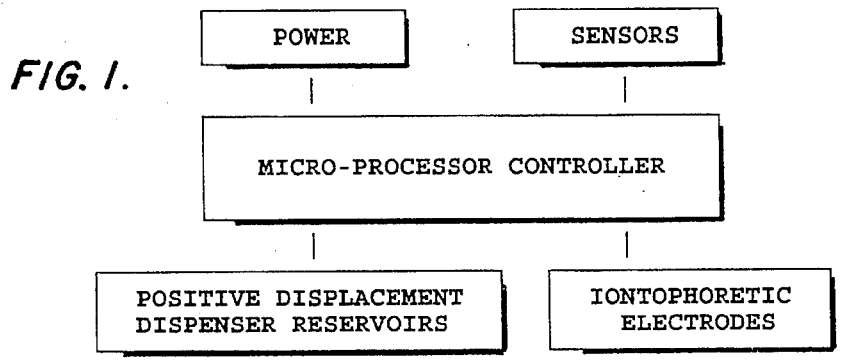
FIG. 1 is a schematic of the preferred embodiment.

Referring now to the drawings, FIG. 1 shows the functional relationship between the controller and the power supply, sensors, positive displacement dispensing reservoirs, and iontophoretic electrodes.

Figure 2:
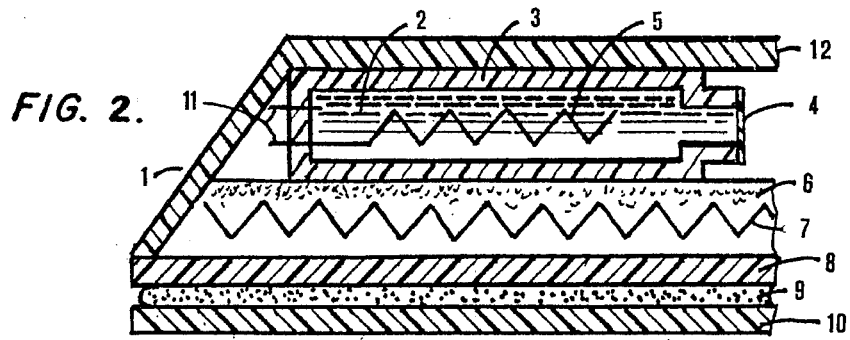
FIG. 2 is a partial section through the preferred embodiment of a transdermal patch.

In FIG. 2 reference numeral 1 identifies a first embodiment which shows the components of said disposable patch comprising a top seal layer 1; one of the segregated reservoirs 2 each having an enclosing wall said reservoirs 2 having at least one closable outlet 4 through which a flowable fluid is induced to administer a medication; and said reservoirs 2 having integral electric resistance heating elements 5 with means for connection 10 to said controller and power source and means for connecting components; and a common reservoir 6 containing an absorbent layer and also containing at least one iontophoretic electrode 7; a semi-permeable membrane 8; an adhesive layer for attachment to the skin 9; and a removable layer 10 to protect said membrane prior to use.

It will be understood by one skilled in the art that the heating wire as shown represents both the shrink dispensing embodiment and the vaporization dispensing embodiment.

It will be understood by one skilled in the art that the reservoir 2 may be embedded in the absorbent layer 5 to protect from premature dispensing due to external pressure and that the shape of the segregated reservoirs 2 may be varied to include freeform and pancake shapes.

Figure 3:
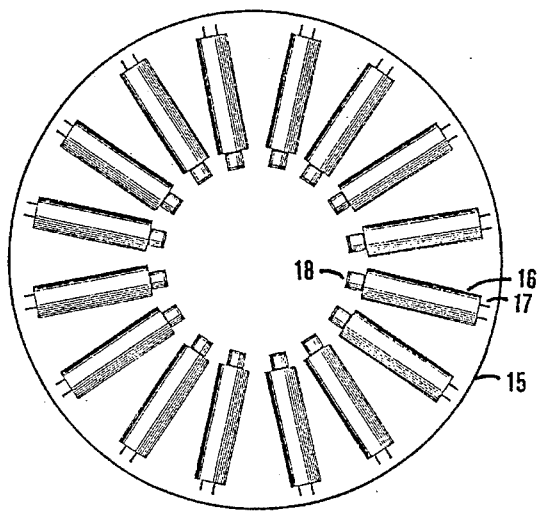
FIG. 3 is a plan view of the preferred embodiment patch with the top seal layer removed to show the multiple reservoir layer.

In FIG. 3 the multiplicity of reservoirs illustrates how various regimens may be administered from within a single transdermal patch. For example, for an acute accident victim in transit, reservoirs in the four quadrants may each respectively contain moisturizing medication, analgesic, tranquilizer, and anticonvulsant. Various drug selections and drug concentrations can be sequenced and controlled by incrementing the multiple reservoirs to meet sensor requirements.

Figure 4:
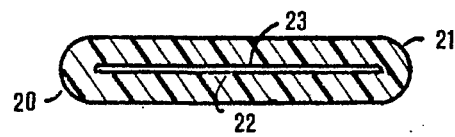
FIG. 4 is a transverse section through a heat shrink reservoir after shrinkage dispensing which reverts to a flat shape for dispensing efficiency.

FIG. 4 is a transverse section through a heat shrink reservoir after shrinkage dispensing which reverts to a flat shape for dispensing efficiency.

Figure 5:
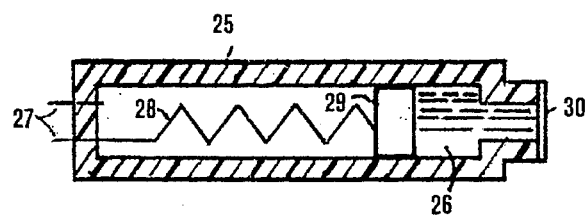
FIG. 5 is a section through a positive displacement dispenser that uses a piezoelectric actuator.

FIG. 5 shows a positive displacement reservoir dispenser 25 with its power leads 27 that are actuated by the microprocessor controller to activate the piezoelectric wire 28 to extend forcing the piston 29 to move toward and force open the closure 30 expelling beneficial fluid 26.

What is claimed as new and desired to be protected by Letter Patent is set forth in the appended claims:

1. A microprocessor controlled transdermal medication patch comprising:

a micro-processor controller circuit;

a battery power source connected to the micro-processor controller to supply electrical power;

user control means connected to the micro-processor controller to enable users to activate or deactivate the transdermal medication patch;

sensing means connected to said micro-processor controller for sensing physiological variables in the body;

connection means for connecting said micro-processor controller circuit to a disposable patch, the patch comprising of:

(1) a top seal layer;

(2) a plurality of segregated reservoirs containing a plurality of beneficial fluids;

(3) at least one common reservoir;

(4) a semi-permeable membrane;

(5) an adhesive layer for attachment to the skin; and (6) a removable layer to protect said membrane and said adhesive layer prior to use; wherein the improvement comprises the addition of positive displacement dispensing means to each of said segregated reservoirs so as to make said patch capable of microprocessor controlled selection for dispensing from among said plurality of beneficial fluids into said common reservoir internal to said patch.

2. The improved patch of claim 1 wherein said segregated reservoirs have at least one closable outlet through which a beneficial fluid is dispensed.

3. The improved patch of claim 1 wherein said common reservoir comprises an absorbent layer of material.

4. The improved patch of claim 1 wherein said segregated reservoirs comprise at least one wall of heat-shrink polymer material, and an electrical resistance heating element which when activated results in a reduction in the interior volume of said reservoir forcing said beneficial fluid through said outlet by positive displacement.

5. The heat-shrink polymer reservoir wall of claim 4 which achieves in its post-dispensing state a relaxed shape in which the opposing internal surfaces are adjacent and parallel so as to minimize any residual undispensed charge.

6. The improved patch of claim 1 wherein said segregated reservoirs comprise an electric resistance heating element which when activated, vaporizes a liquid, expelling said flowable fluid by said positive displacement.

7. The improved patch of claim 1 wherein said segregated reservoirs contain a piezoelectric driven piston to dispense said beneficial fluid by said positive displacement.

8. The improved patch of claim 1 wherein said segregated reservoirs comprise an electric solenoid to dispense said beneficial fluid by said positive displacement.

9. The improved patch of claim 1 wherein said common reservoir comprise at least one iontophoretic electrode.

* * * * *